United States Patent [19]

Drewlow

[11] Patent Number: Plant 7,316

[45] Date of Patent: Sep. 4, 1990

[54] POINSETTIA PLANT NAMED YULETIDE

[75] Inventor: Lyndon W. Drewlow, Ashtabula, Ohio

[73] Assignee: Mikkelsens, Inc., Ashtabula, Ohio

[21] Appl. No.: 355,183

[22] Filed: May 22, 1989

[51] Int. Cl.[5] ..... A01H 5/00
[52] U.S. Cl. ..... Plt./86
[58] Field of Search ..... Plt./86

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Poinsettia plant named Yuletide originated from grafting the cultivar Super Rochford, known for its excellent branching, to the cultivar Merrimaker, known for its color intensity and bract quantity. Yuletide is characterized by its intense rich red bract color, excellent branching, compact habit, early flower initiation, non-splitting cyathia which are retained under stress, and its tolerance to conditions of low light and high temperature.

1 Drawing Sheet

The present invention relates to a new and distinct cultivar of Poinsettia plant, botanically known as *Euphorbia pulcherrima,* and referred to by the cultivar name Yuletide. The new cultivar was developed by me by grafting the excellent branching type cultivar Super Rochford (unpatented) to the non-branching cultivar Merrimaker (U.S. Plant Pat. No. 6,097) in an attempt to transfer the branching habit of Super Rochford to Merrimaker. The graft was successful, resulting in the new cultivar having the desired branching habits of Super Rochford while retaining the desirable characteristics of Merrimaker of bract quantity and color intensity. Asexual reproduction of stem cuttings has shown that the unique features of this new Poinsettia are stabilized and are reproduced true to type in successive propagations.

The following characteristics distinguish the new Poinsettia from both its parent cultivars and other cultivated Poinsettia of this type known and used in the floriculture industry. Comparisons are made to the parent cultivars.

1. When 5 or more nodes are left after a pinch (apical tip removal) Yuletide will develop a shoot from each node left like Super Rochford, while Merrimaker will develop a shoot only from the upper 2 or 3 nodes.

2. Yuletide plants are shorter than Merrimaker plants after pinching of similar sized plants because there is less apical dominance in the branched type. Thus, all shoots develop to the same height instead of 2 or 3 shoots growing very tall. Super Rochford is taller than Yuletide even though it also branches from every node.

3. Yuletide has slightly lighter green leaves than Merrimaker and Super Rochford.

4. Bract coloration of Yuletide is a shade lighter red than Merrimaker but still is a very intense rich red. It is a much deeper red than Super Rochford.

5. Yuletide appears to be more tolerant to low light levels and high temperature conditions of the average home as leaves do not yellow and drop like Merrimaker under these conditions when the plant is kept moist. This characteristic is similar to Super Rochford which has excellent foliage retention.

6. All other significant characteristics of Yuletide are similar to Merrimaker, such as early flower initiation under natural short days, no signs of epinasty (leaf petiole twisting), similar shaped leaves and bracts, retention of the cyathia under stress conditions, and cyathias which do not split.

7. Yuletide appears to be less susceptible to delay of flower bud initiation under high night temperature conditions (above 21°), like Merrimaker, while Super Rochford shows heat delay at these temperatures.

The accompanying colored photograph illustrates in top perspective view the overall appearance of Yuletide, showing the colors as true as it is reasonably possible to obtain in a colored reproduction of this type. The photo was taken in December, 1988.

The following is a detailed description of my new Poinsettia cultivar based on plants produced under commercial practices in Ashtabula, Ohio under greenhouse conditions. Color references are made to The Royal Horticultural Society Colour Chart except where general terms of ordinary dictionary significance are used.

Origin: Graft induced change from non-branching to branching of the original cultivar Merrimaker.

Propagation:

(A) *Type cutting.*—Stems 5 to 6 cm in length.

(B) *Time to root.*—14 days at 21° C. summer, 18 days at 21° C. winter.

(C) *Rooting habit.*—Abundant and fibrous.

Plant Description:

(A) *Form.*—Upright; when apical meristem is removed (pinching) leaving 5–6 nodes above the soil line of pot, generally all lateral shoots will emerge and develop.

(B) *Habit of growth.*—Strong, thick stems that hold the bracts up for good flowering display. Growth is vigorous, and depending on scheduling system, plants may need an application of a chemical growth regulator such as Cycocel. Nodal connection of stems is strong enough to hold up bracts without breaking.

(C) *Foliage Description.*—Leaves are alternate and borne on 5–6 cm long petioles that are purple-red in color. (1) Size: Mature leaves are 13 to 14 cm long by 9 to 10 cm wide at broadest area. (2) Shape: Leaf shape is variable from ovate to hastate with an acute apex and rounded base. (3) Texture: Upper surface glabrous, lower glabrous and rugose because of protruding veins. (4) Margin: Entire, but some leaves are large lobed. (5) Color: Young foliage, top side 144A, under side 144A. Mature foliage, top side 137A, under side 137C.

Flowering Description:

(A) *Flowering Habits.*—Earlier flowering than most commercial cultivars, apparently having a longer critical day length for flower initiation. Under controlled day length, development time is approximately 10 weeks. Flowers earlier, like Merrimaker, than most commercial cultivars under natural day length in Ohio, but takes approximately the same time to develop when tested under exact controlled day lengths with other commercial cultivars. The characteristic of earlier flower initiation is of significant commercial importance.

(B) *Natural flowering season.*—November 15 to 25 under Ohio conditions.

(C) *Cyathia description.*—Are very stress tolerant, remaining in the involucre for a considerable time under low light, high temperature conditions; severe drying causes them to drop; involucre is almost flat with only slight reflexing.

(D) *Cyathia borne.*—Stay closely clustered for a considerable time without growing apart (splitting); flowering can be initiated any time of the year by controlling day length; cyathia will continue to initiate until day length is greater than approximately 13 hours and temperature is above 27° C.

(E) *Quantity of cyathia.*—Is highly dependent on cultural practices and varies from minimum of 8 to 10 to as many as 50; cyathia will continue to develop from November-April resulting in the large number (F) *Bracts.*—(1) Shape: ovate; mature 11 to 12 cm long; 8 to 9 cm wide on a pinched plant; petioles 2 cm long. (2) Color at maturity: deeper than 42A but not as deep red as 45B. Young bract: 42A. Under side: young bracts red with green areas; mature 47B, veins red. (3) Number of bracts: up to 50 or more depending on growing conditions; bract size can vary with growing conditions, whether the plant was pinched, and use of growth regulator; the last true leaves tend to become red.

(G) *Reproductive organs.*—(1) Stamens: numerous. (a) Anther shape: oblong, yellow in color with red tint. (b) Filament color: red. (c) Pollen color: yellow. (2) Pistils: (a) Stigma shape: forked, reddish-purple in color. (b) Style color: whitish green. (c) Ovaries: 3, celled, 4 mm, yellow green in color, below receptive stigma. (3) Nectar cups: 1 or 2 on each cyathia; yellow in color with tint of red; nectar is usually readily available on maturing cyathia.

Disease resistance: There is an apparent lack of preference to white fly, as heavily infested adjacent cultivars did not cause buildup of egg masses on Yuletide.

I claim:

1. A new and distinct cultivar of Poinsettia plant named Yuletide, as illustrated and described.

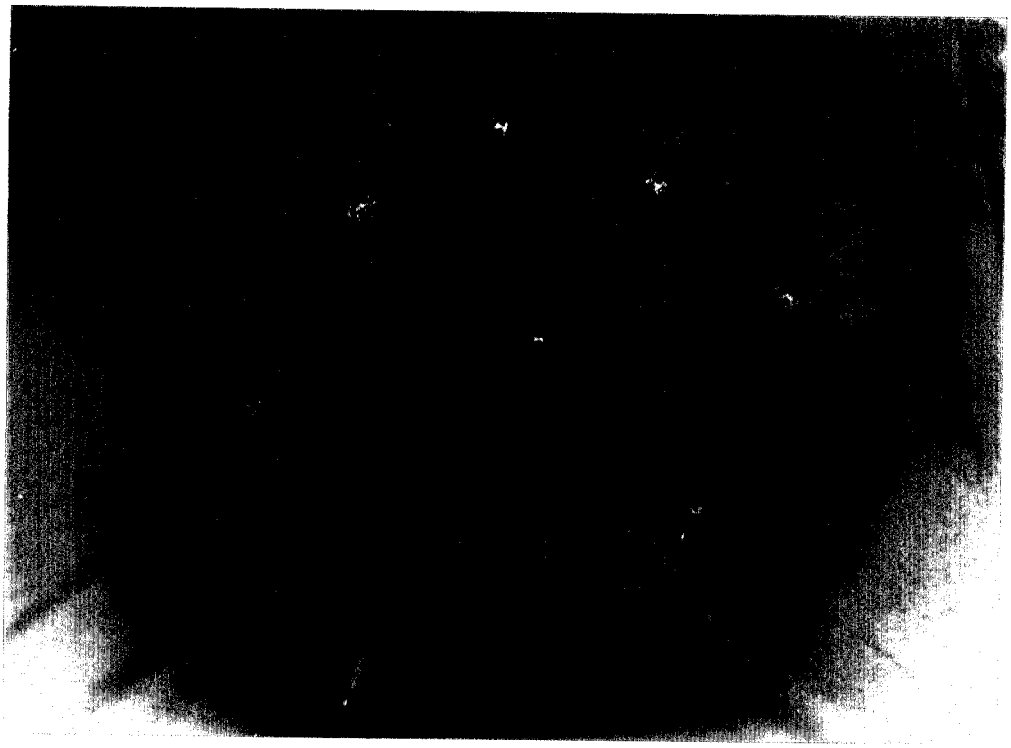

* * * * *